United States Patent [19]

Nemeth

[11] 4,178,933
[45] Dec. 18, 1979

[54] EXTRACTIVE TRANSFER DIAPER TAB MEANS

[75] Inventor: Suzette B. Nemeth, Painesville, Ohio

[73] Assignee: Avery International Corporation, San Marino, Calif.

[21] Appl. No.: 780,411

[22] Filed: Mar. 23, 1977

[51] Int. Cl.² .............................................. A61F 13/16
[52] U.S. Cl. ............................ 128/284; 128/DIG. 30; 24/DIG. 11
[58] Field of Search .............. 24/73 V, 67 R, 67 AR, 24/7, DIG. 11; 128/DIG. 30, 289, 287, 284

[56] References Cited

U.S. PATENT DOCUMENTS

| | | | |
|---|---|---|---|
| 3,616,114 | 10/1971 | Hamaguchi | 128/287 |
| 3,951,149 | 4/1976 | Ness | 128/287 |
| 4,020,842 | 5/1977 | Richman et al. | 128/284 |
| 4,050,121 | 9/1977 | Richman | 128/287 |

Primary Examiner—Robert W. Michell
Assistant Examiner—M. A. Juten
Attorney, Agent, or Firm—Pearne, Gordon, Sessions

[57] ABSTRACT

A diaper tab stock of only two substrates provides diaper tabs that are linerless, that are refastenable, and that are of the relatively strong Y-configuration type. When tabs made from the stock are closed and reopened in the normal manner of use, part of one adhesive layer is "extractively transferred" from between the two substrate layers to another part of the diaper to thereby present a "fresh" adhesive face for subsequent refastening, such transfer occurring in the absence of any transfer of a substrate. The two-substrate construction may be formed by folding an appropriately coated originally single layer of substrate material.

3 Claims, 7 Drawing Figures

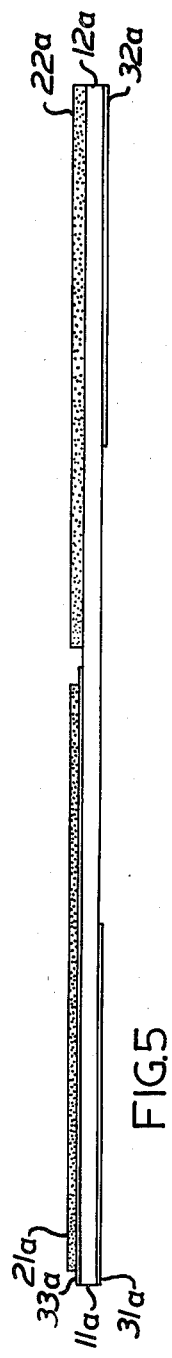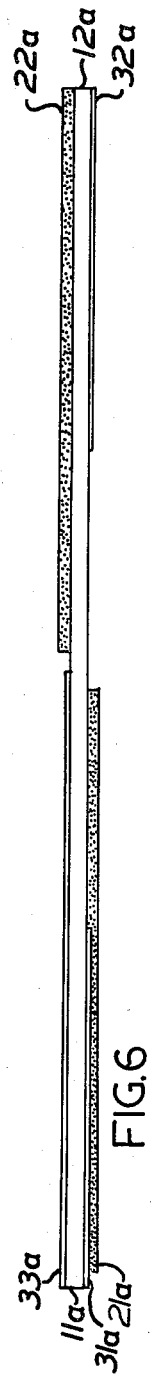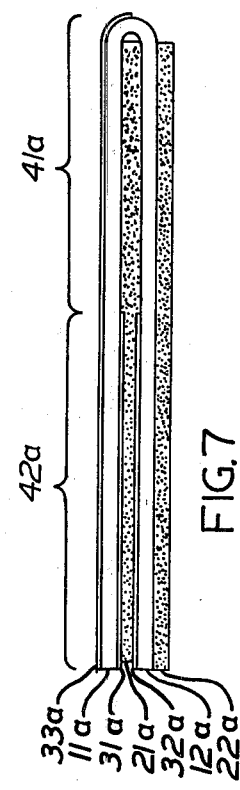

EXTRACTIVE TRANSFER DIAPER TAB MEANS

This invention relates to web constructions of tab stock of the kind adapted to be supplied to a diaper manufacturer and to be separated by the manufacturer into individual linerless refastenable diaper tab constructions of Y-configuration and applied to individual diapers, usually two tabs to a diaper. By "linerless" is meant the absence of any adhesive-protecting liner of release paper or the like that has to be separately disposed of by the person applying the diaper. By "refastenable" is meant a diaper tab which can be fastened by exposing and applying an adhesive face and refastened by exposing and applying a "fresh" second adhesive face.

Linerless refastenable tab constructions are shown in the following:

| | | | |
|---|---|---|---|
| 3,951,149 | 4/1976 | Ness et al. | Johnson & Johnson |
| Appln. Serial No. 624,870 | Filed 10/23/75 | Richman et al. | Avery International Corporation (common assignee) |
| Appln. Serial No. 770,646 | Filed 2/22/77 | Nemeth | Avery International Corporation (common assignee) |

However these tab constructions all require at least two substrates to provide for refastenability. One substrate is associated with the initially exposed adhesive and the other substrate is associated with the subsequently exposed "fresh" adhesive. The substrate associated with the initially exposed adhesive is either not originally co-extensive with the other substrate to thereby allow the former to transfer along with the originally exposed adhesive (Ness), or is slit to allow part of such first-mentioned substrate to transfer along with the originally exposed adhesive (Richman, Nemeth), the referred-to transfer in each case being from the part of the diaper the mentioned elements are first associated with to another part.

Where a refastenable tab of Y-configuration is provided, as in the second of the above items, three tab substrates are required, two for the refastenable feature, and an additional one for the Y-configuration feature. By "Y-configuration" is meant a tab configuration in the shape of a Y whose two legs and stem all bear adhesive, the legs being adapted to be fastened by the manufacturer to both sides of one part of a diaper adjacent an edge, and the stem being adapted to be fastened to another part of the diaper by a person applying the diaper. Tabs of Y-configuration provide increased or double strength where it is most needed—at the diaper-to-tab connection which receives the strain when the person applying the diaper pulls on the tab to draw the diaper tight before closing it.

The present invention provides a linerless refastenable diaper tab of Y-configuration which is so arranged as to require only two substrates even though both the refastenability and Y-configuration features are included. This is accomplished by providing for successive partial peeling back between a certain adhesive layer and two different substrates between which the adhesive is sandwiched. The arrangement is such that after the first partial peeling back and upon the first closing of the diaper by conventional manipulation of the tab by the user, adherence to the diaper of the adhesive face exposed by the first partial peeling back assures exposure of the second adhesive face during a subsequent second partial peeling back when the diaper is first reopened. The two substrates may be originally coextensive but neither need be slit.

The portion of the adhesive layer that is associated with peeling back (the peelback portion) separates or breaks from the portion that is not so associated as the second peeling back is completed, allowing the reopening of the diaper to be completed. At this point the peelback portion of the adhesive layer in question is left deposited on one portion of the diaper and completely disassociated from the remainder of the tab structure while the other portion of such adhesive layer remains between and permanently associated with the two different substrates between which it was initially sandwiched, continuing to fix them together.

All portions of the two substrates remain at all times with the part of the diaper on which they are originally mounted even though the adhesive originally between them at the peelback portion becomes completely disassociated from such part of the diaper when the diaper is opened. Consider the substrate-adhesive-substrate construction just discussed as a "sandwich" in which the substrates are the "bread" and the adhesive is the "meat." All the "bread" and roughly half the "meat" remains on one part of the diaper while the other half of the "meat" is extracted or is taken out from between the "bread" and transferred or put on the other part of the diaper in the course of closing and reopening the diaper. This type of extractive transfer of part of an adhesive layer from between two substrates which remain permanently joined by the remaining part of the adhesive layer is believed to be completely novel in diaper closures.

In the drawings, the thicknesses of the webs and coatings are greatly exaggerated.

FIG. 5 is a schematic transverse cross-section of another form of diaper tab stock at a stage during the manufacture thereof.

FIG. 6 is a similar view of the same stock after it has been self-wound and then unwound.

FIG. 7 is a schematic transverse elevation of a diaper tab constructed according to the invention by folding together the two ends of the construction shown in FIG. 6.

Figure 1:
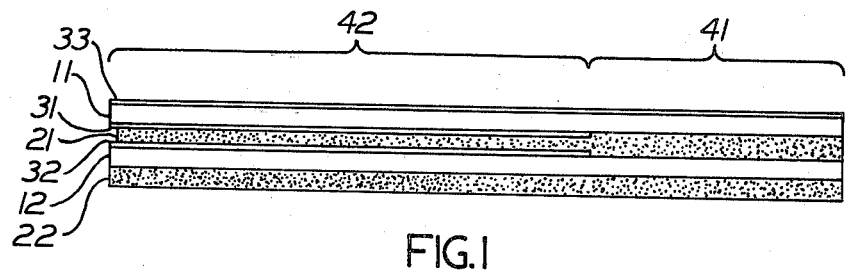
FIG. 1 is a schematic transverse elevation of diaper tab stock constructed according to the invention and then cut transversely to machine direction (machine direction being into the paper) into an individual laminate.

As seen in FIG. 1, the web construction comprises a first substrate 11, extending, transversely to machine direction, along first and second length portions 41 and 42 respectively. The first substrate bears first substrate adhesive 21 on its underside. Preferably, the adhesive 21 stops short of the free end of the first substrate 11 at the second length portion as seen in FIG. 1.

A second substrate 12 also extends along the length portions 41 and 42. The second substrate bears the second substrate adhesive 22 on its underside. The second substrate adhesive 22 extends along the first and second length portions 41 and 42, as shown.

First and second release means 31 and 32 are provided for the first substrate adhesive 21 and are located respectively above and below the first substrate adhesive at the second length portion 42, as seen in FIG. 1. The first length portion 41 is substantially free of both the first and second release means 31 and 32. The first release means 31 is on the underside of the first substrate 11 and the second release means 32 is on the topside of the second substrate 12. The second release means 32 is selected to provide relatively easier release than the first release means 31.

In order that the stock shown in FIG. 1 may be self-wound, a third release means 33 is provided on the topside of the substrate 11. The third release means 33 is also selected to provide relatively easier release than the first release means 31.

Figure 2:
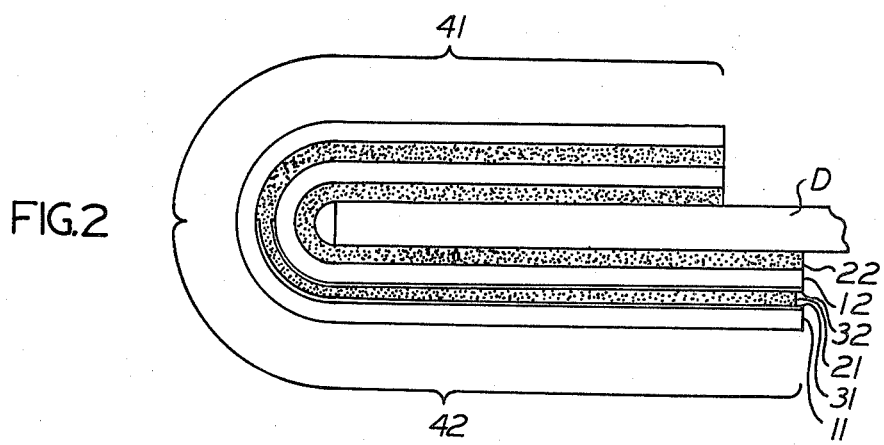
FIG. 2 is a view of the laminate shown in FIG. 1 as folded and fastened at one edge of one portion of a diaper by the diaper manufacturer.

The construction in the form described and shown in FIG. 1 can be supplied to a diaper manufacturer as a self-wound roll of diaper tab stock. The diaper tab manufacturer cuts the roll of diaper tab stock transversely and folds the first and second length portions around the edge of the diaper D, as seen in FIG. 2, applying the second substrate adhesive 22 to the diaper to anchor the tab in mounted condition. The first substrate adhesive 21 remains positioned between the substrates 11 and 12 at the length portion 42 as well as at the length portion 41.

As previously indicated, the invention involves extractive transfer of the second length portion of the adhesive layer 21 from between the substrates 11 and 12 as an incident of the normal usage of the mounted tab by a parent who fastens and then unfastens the diaper. Thus the second length portion 42 of the adhesive layer 32, which is between the substrates 11 and 12 as seen in FIG. 2, is subsequently extracted from between the two substrates and away from both of them to be transferred to another part of the diaper, as seen in FIG. 4.

Thus, when the diaper is first being applied on an infant, the second length portion of the substrate 11 is unfolded. Because the second release means 32 provides a relatively easier release than the first release means 31, the first substrate adhesive 21 peels back with the substrate 11 to be thereby exposed at face 51 for joinder to another part of the diaper when, as seen in FIG. 3, the diaper is fastened by the tab.

Figure 4:
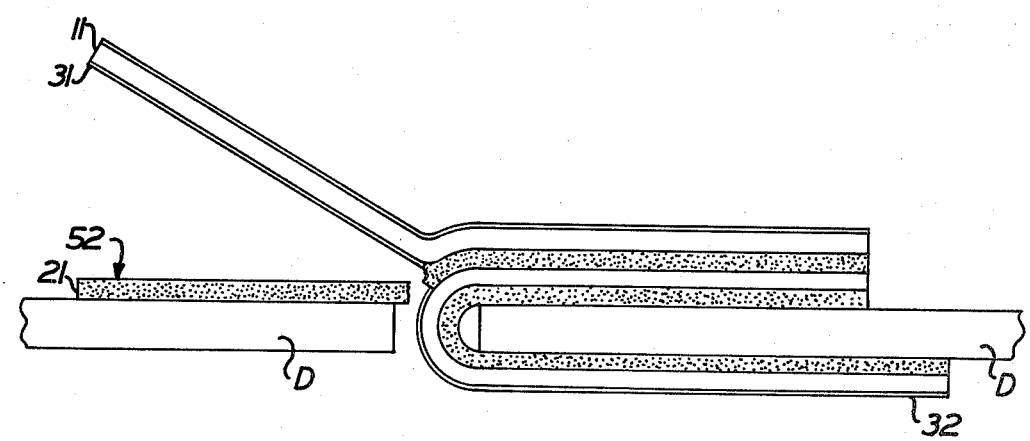
FIG. 4 is a view similar to FIG. 3 showing the configuration of the parts at the moment of unfastening of the diaper tab following its initial fastening.

When the diaper is subsequently unfastened by peeling back the second length portion of the substrate 11 from the portion of the diaper (the leftward portion of the diaper as seen in FIG. 4) to which it is attached, the first release means 31 allows the second length portion of the substrate 11 to peel back from the adhesive 21. When the peel-back progresses beyond the leftward portion of the diaper D, the peel-back force is no longer resisted by any part of the diaper, but only by a thin cross-section of the adhesive layer 21. The adhesive layer 21 thereupon ruptures in the vicinity of the boundry between the first and second length portions 41 and 42 thereby completing the transfer of the second length portion of the adhesive 21 to the leftward portion of the diaper D, i.e., the portion with which the illustrated tab was not originally associated when it was attached to the diaper by the manufacturer. This completion of transfer is illustrated in FIG. 4. Face 52 of the second length portion of adhesive 21 is thereby exposed for the first time and provides a "fresh" adhesive face for subsequent refastening of the tab.

Figure 3:
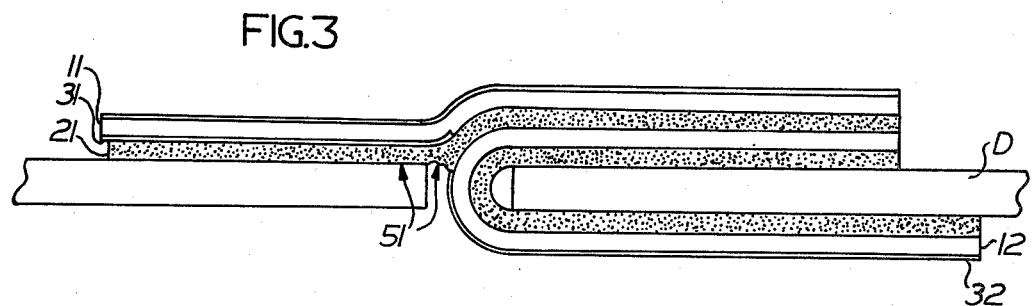
FIG. 3 is a view of the same laminate, now unfolded to join the tab to another portion of the diaper.

When the second length portion of the adhesive 21 positioned as in FIG. 4, the diaper may be reclosed by again positioning the second length portion of the substrate 11 on the fresh face 52 of the adhesive 21 so that the parts resume a relationship similar to that shown in FIG. 3 but of course with the first and second length portions of the adhesive 21 remaining separated by the rupture which occurs incident to the first reopening of the tab as above described. If it is desirable to tighten the tab fastening upon reclosing, as is ordinarily the case, this can be done by drawing the second length portion of the substrate 11 somewhat further to the left than the second length portion of the adhesive 21, so that these second length portions only partially overlap. If necessary, the righthand portion of the diaper shown in the drawings can be overlapped somewhat with the lefthand portion to accomplish this tightening, it being understood that the thicknesses of the tab elements shown in the drawings are greatly exaggerated and will not in fact interfere with overlapping.

It will be understood that the release means, and particularly the release means 31, may be of any conventional type which allows peel-back release but strongly resists shear loads distributed over the interface between the release coat and an adjacent adhesive layer. Such shear loads are, of course, imposed by fastening tension between the two parts of the diaper shown in the drawing.

The two different substrates used according to the invention may be either completely separate layers, or they may be separate layers hinged together at one edge by virtue of having been formed from a single layer folded over on itself in the general manner of the prior invention taught in Application Ser. No. 757,910 filed Jan. 10, 1977, of common assignee. The formation of a construction embodying the present invention from an originally single flat layer of substrate material is illustrated in FIGS. 7–9. This aspect of the present invention represents an improvement over the just mentioned prior invention in that such prior invention does not teach the concept of extractive transfer of part of an adhesive layer and does not provide a "refastenable" diaper tab as above defined.

The construction illustrated in FIG. 7 will be seen to be very similar to that illustrated in FIG. 1 except that the first and second substrates 11a and 12a illustrated in FIG. 7 are in fact hinged together by folding the initially single layer seen in FIGS. 5 and 6.

In other respects the elements and length portions labelled in FIG. 1 may be substantially duplicated by those of FIG. 7. Thus in FIG. 7 are seen first and second substrates 11a and 12a, first and second substrate adhesives 21a and 22a, first, second, and third release means 31a, 32a, and 33a, and first and second length portions 41a and 42a.

The single substrate layer which is to be subsequently folded into the two substrate layers 11a and 12a may be coated by the diaper tab stock manufacturer in the manner shown in FIG. 5. When the illustrated construction is self-wound for shipment and storage and subsequently unwound by a diaper manufacturer for formation into tabs, the first adhesive coating 21a transfers from the position shown in FIG. 5 to that shown in FIG. 6 because the third release means 33a provides relatively easier release than the first release means 31a. The diaper manufacturer can then fold the single substrate together to change the cross section from that shown in FIG. 6 to that shown in FIG. 7 and can transversely sever the tab stock to form individual diaper tabs. The diaper tab shown in FIG. 7 is then folded around the edge of the diaper (not shown) in a manner substantially identical to that illustrated in FIG. 2.

The invention is not limited to the precise details of the constructions shown, but covers all variants based on the invention. For example, the second substrate adhesive 22 may be omitted at parts of the first and second length portions, one appropriate place for omission being in the region of the boundary between the length portions. The invention is defined by the following claims:

What is claimed is:

1. A diaper having a linerless refastenable two-substrate diaper tab formed of diaper tab stock comprising a web construction made up of initially flat but flexible substrate material and suitable to be formed in long passes along the machine direction of a coating and laminating line and to be rolled up for storage and shipment, and unrolled for use by diaper manufacturers, and fabricatable for storage and shipment completely by web coating and web-to-web laminating operations and without the necessity for folding or slitting operations, and suitable for high speed dispensing on automatic equipment, said tab including a first substrate extending, transversely to machine direction, along first and second length portions and bearing first substrate adhesive on its underside at both said length portions, a second substrate extending along said first and second length portions and bearing second substrate adhesive on its underside at both said first and second length portions, first and second release means for said first substrate adhesive being located respectively above and below said first substrate adhesive at said second length portion, said first length portion being substantially free of both first and second release means, said first release means being on the underside of said first substrate and said second release means being on the topside of said second substrate, said second release means having physical and structural characteristics for providing a release from said first substrate adhesive at a lower separating force level than that required by the physical and structural characteristics of said first release means, the tab initially being applied to one edge of a diaper with the first length portions of the second substrate adhesive, second substrate, first substrate adhesive, and first substrate respectively layered on one side of said one diaper edge and with the second length portions of the second substrate adhesive and second substrate, the second release means, the second length portion of the first substrate adhesive, the first release means and the second length portion of the first substrate respectively layered on the opposite side of said one diaper edge, whereby when the tab, mounted on said one edge of the diaper, is manipulated in the normal manner by a person who fastens and then unfastens the diaper by separating the second length portion of the first substrate adhesive, first release means, and second length portion of the first substrate from the second release means and applying the same to another part of the diaper for fastening and then removing the first release means and second length portion of the first substrate for unfastening, the part of said first substrate adhesive that is at said second length portion being exclusively extractively transferred from between said first and second substrates and from said second length portion of said first substrate permanently to said other part of the diaper.

2. A construction as in claim 1, including a third release means on the topside of said first substrate, said third release means providing relatively easier release than said first release means.

3. A construction as in claim 1, said first and second substrates being hinged together at the endmost edge of said first length portion.

* * * * *